(12) United States Patent
Guo et al.

(10) Patent No.: US 9,944,915 B2
(45) Date of Patent: Apr. 17, 2018

(54) CELLULASE HAVING IMPROVED THERMOSTABILITY

(71) Applicant: DONGGUAN APAC BIOTECHNOLOGY CO., LTD., DongGuan (CN)

(72) Inventors: Rey-Ting Guo, Taipei (TW); Ya-Shan Cheng, Taipei (TW); Jian-Wen Huang, Taipei (TW); Tzu-Hui Wu, Taipei (TW); Hui-Lin Lai, Taipei (TW); Cheng-Yen Lin, Taipei (TW); Tsung-Yu Ko, Taipei (TW)

(73) Assignee: DONGGUAN APAC BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 15/381,438

(22) Filed: Dec. 16, 2016

(65) Prior Publication Data
US 2017/0183641 A1   Jun. 29, 2017

(30) Foreign Application Priority Data

Dec. 23, 2015  (TW) .............................. 104143261 A

(51) Int. Cl.
*C12N 9/24* (2006.01)
*C12N 15/56* (2006.01)
*C12N 9/42* (2006.01)

(52) U.S. Cl.
CPC .... *C12N 9/2437* (2013.01); *C12Y 302/01004* (2013.01)

(58) Field of Classification Search
None
See application file for complete search history.

(56) References Cited

U.S. PATENT DOCUMENTS

2014/0308713 A1* 10/2014 Lee .................. C12P 19/14
435/99
2015/0050701 A1*  2/2015 Trudeau ......... C12Y 302/01091
435/99
2016/0326507 A1* 11/2016 Lavigne ............... C12N 9/244

OTHER PUBLICATIONS

Badieyan et al., Study and design of stability in GH5 cellulases, Biotechnol. Bioeng., 2012, 109, 31-44.*
Dombkowski et al., Protein disulfide engineering, FEBS Lett., 2014, 588, 206-12.*

* cited by examiner

*Primary Examiner* — Robert B Mondesi
*Assistant Examiner* — Todd M Epstein
(74) *Attorney, Agent, or Firm* — Kirton McConkie; Evan R. Witt

(57) ABSTRACT

A cellulase having improved thermostability is disclosed. The cellulase comprises a modified amino acid sequence of SEQ ID NO: 2, wherein the modification is adding a cysteine in N terminal and adding a glycine and a cysteine or adding a proline and a cysteine in C terminal.

6 Claims, 8 Drawing Sheets

FIG. 1

| Primer Pair I | Primer Sequence |
|---|---|
| C1 F | 5'- GCTGAAGCTGAATTCTGTGGTGTTAGATTTGCTG -3' (SEQ ID NO: 7) |
| C1 R | 5'- CAGCAAATCTAACACCACAGAATTCAGCTTCAGC -3' (SEQ ID NO: 8) |

FIG. 2

| Primer Pair II | Primer Sequence |
|---|---|
| G329C330 F | 5'- TTGTTTGGCAAGAAAGGGTTGTTAAGCGGCCGCCAGCTTTC -3' (SEQ ID NO: 9) |
| G329C330 R | 5'- GAAAGCTGGCGGCCGCTTAACAACCCTTTCTTGCCAAACAA -3' (SEQ ID NO: 10) |

FIG. 3

| Primer Pair III | Primer Sequence |
|---|---|
| P329 F | 5'- TTGTTTGGCAAGAAAGCCATGTTAAGCGGCCGCCA -3' (SEQ ID NO: 11) |
| P329 R | 5'- AAAGCTGGCGGCCGCTTAACATGGCTTTCTTGCCA -3' (SEQ ID NO: 12) |

- SEQ ID NO: 3
- SEQ ID NO: 4

FIG. 6

CELLULASE HAVING IMPROVED THERMOSTABILITY

FIELD OF THE INVENTION

The present invention relates to a cellulase, and more particularly to a cellulase having improved thermostability.

BACKGROUND OF THE INVENTION

Cellulose is one of the major components in plant cell wall and is also a major resource of biomass on earth. Hence, many enzymes that degrade cellulose can be widely applied in many different industries. Cellulose is a polysaccharide composed of glucose units linked by β-1,4-glycosidic bond. These polysaccharides organize tightly together to form crystalline cellulose in order to defense destructing energy from outside of plant. On the other hand, many kinds of herbivores and microbes need to degrade cellulose from plant to glucose as an energy source by different degrading enzymes including cellulase, xylanase and so on. The catalytic mechanism of cellulase involves hydrolyzing the β-1,4-glycosidic bond between two sugar units by acid-base interaction. Cellulase can be generally divided into three groups including endoglucanase, cellobiohydrolase and β-glucosidase. Endoglucanase can randomly degrade cellulose into many small fragments. Cellobiohydrolase can degrade cellulose from reducing end or non-reducing end to release main product, cellobiose. β-Glucosidase can degrade cellobiose into simple sugar glucose.

So far, the industrial applications of cellulase are widespread in food industry, feed industry, textile industry or paper pulp industry, even in biofuel production. In general, cellulase needs to conform to different appropriate conditions according to different industrial needs. For example, acidic and thermostable enzymes are suitable for the feed industry but textile industry prefers alkaline enzymes. Therefore, scientists always try to seek better enzymes which are more suitable for different industrial needs in academic or industrial researches. Currently, many researchers and enzyme companies could produce better enzymes by screening in nature or modifying present enzymes. There are generally two strategies of enzyme modification including directed evolution that randomly mutates the enzyme gene and selects with desirable properties or rationale engineering that specifically mutates the enzyme gene based on the structural information of the enzyme.

Different industrial production processes need different appropriate enzymes to cooperate and participate in their production procedures. Despite cellulase has been applied in industry for a long time, many industrial cellulases which are produced from mesophile such as *Trichoderma reesei* have worse thermostabilities. On the other hand, thermostable cellulase can be efficiently applied in the industry which needs high temperature reaction condition, such as brewing, bioethanol production and so on. Thermostable enzyme has higher protein stability, so it can be stable and even work better in high temperature condition. In addition, to increase enzyme activity is also a key point for the improvement of industrial enzyme. Higher enzyme activity represents the cost down and the companies will have better profit.

According to previous studies, disulfide bonds are beneficial to protein stability and thermostability. *Trichoderma reesei* has many kinds of cellulases, in which the cellulase Cel5A belonging to GH family 5 and whose protein structure (ID 3QR3) had been published in 2011 has four disulfide bonds at positions C16-C22, C92-C99, C232-C2683 and C273-C323, and thus has high melting temperature (Tm). Cel5A belongs to α/β TIM-barrel protein (Toni M Lee, Mary F Farrow, Frances H Arnold, and Stephen L Mayo. (2011) Protein Structure Report, November27; 20(11):1935-40). In 2004, Simon R. Andrews et al. found that adding disulfide bonds at N terminals and C terminals of the xylanase CjXyn10A of *Cellvibrio japonicas* and the xylanase CmXyn10B of *Cellvibrio mixtus* had increased the protein stability and further increased the protein thermostability, and both CjXyn10A and CmXyn10B belong to α/β TIM-barrel proteins (Andrews S. R., Taylor E. J., Pell G., Vincent F., Ducros V. M., Davies G. J., Lakey J. H., and Gilbert H. J., (2004) J. Biol. Chem. December 24;279(52): 54369-79).

Therefore, the present invention intends to add disulfide bonds of a cellulase by gene modification, so as to increase the thermostability and further increase the industrial value of the cellulase.

SUMMARY OF THE INVENTION

An object of the present invention is to modify a cellulase by means of structural analysis and site-directed mutagenesis for adding disulfide bonds of the cellulase, so as to efficiently increase the thermostability and further increase the industrial value of the cellulase.

According to an aspect of the present invention, there is provided a cellulase comprising a modified amino acid sequence of SEQ ID NO: 2, wherein the modification is adding a cysteine in N terminal and adding a glycine and a cysteine or adding a proline and a cysteine in C terminal.

In an embodiment, a gene encoding the amino acid sequence of SEQ ID NO: 2 is isolated from *Trichoderma reesei* and optimized.

In an embodiment, the cellulase has a full length amino acid sequence of SEQ ID NO: 4.

In an embodiment, the cellulase has a full length amino acid sequence of SEQ ID NO: 6.

According to another aspect of the present invention, there is provided a nucleic acid encoding the aforesaid cellulase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild type cellulase;
FIG. 2 shows the primer sequences of the primer pair I;
FIG. 3 shows the primer sequences of the primer pair II;
FIG. 4 shows the primer sequences of the primer pair III;
FIG. 5 shows the nucleotide sequence and the amino acid sequence of the CGC cellulase;
FIG. 6 shows the nucleotide sequence and the amino acid sequence of the CPC cellulase.

DETAILED DESCRIPTION OF THE PREFERRED EMBODIMENT

Figure 7:
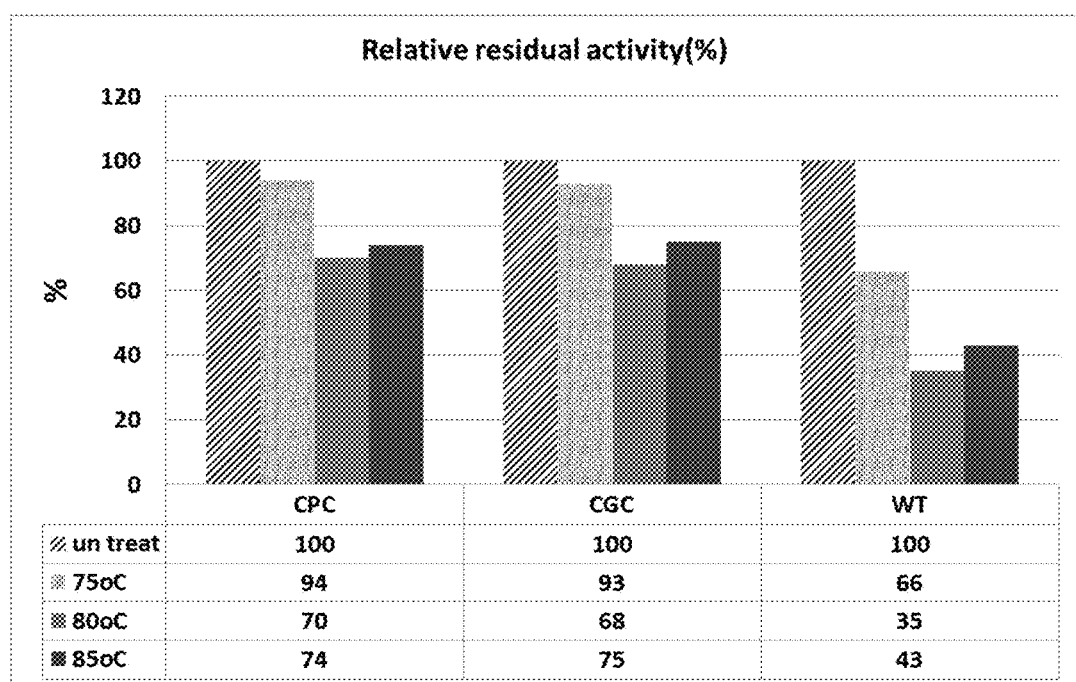
FIG. 7 shows the thermostability analysis of the wild type cellulase, the CGC cellulase and the CPC cellulase.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
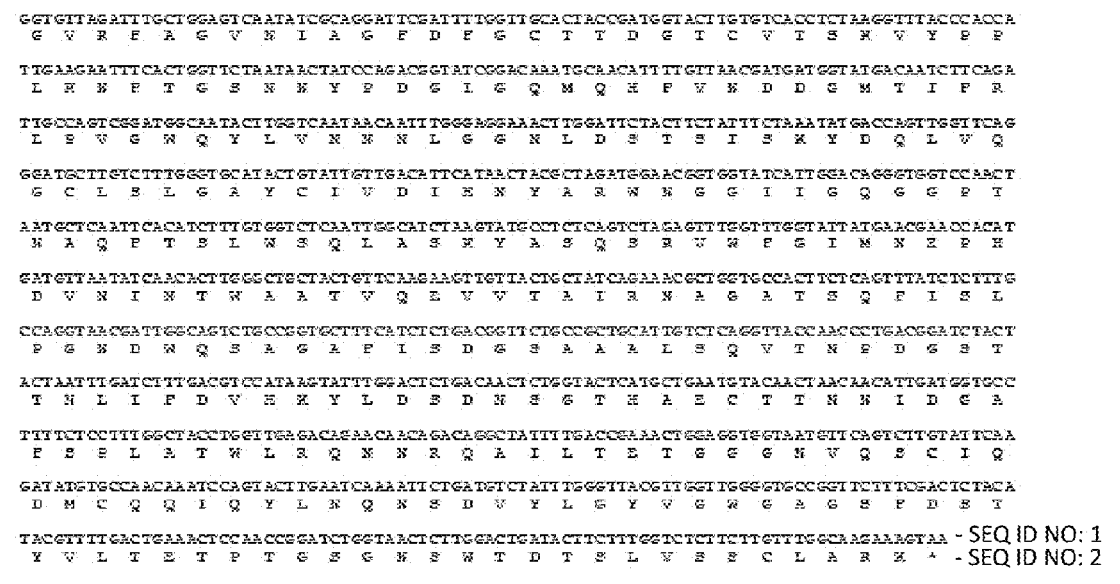

The cellulase employed in the present invention is encoded by a gene isolated from *Trichoderma reesei*, and the gene is optimized to remove 91 amino acids in the N terminal of the protein to enhance the protein expression. The gene is not mutated and thus is called the wild type (WT) cellulase in the present invention. The wild type cellulase gene was constructed into pPICZαA vector by EcoRI and NotI, and was checked by DNA sequencing and then expressed. FIG. 1 shows the nucleotide sequence and the amino acid sequence of the wild type cellulase, wherein the wild type cellulase gene consists of 984 base pairs (SEQ ID NO: 1, including the stop codon) and encodes 327 amino acids (SEQ ID NO: 2).

The protein structure of the wild type cellulase was further analyzed by PyMOL. It was found that the spatial distance between the N terminal and the C terminal of the wild type cellulase is about 11.3 Å, which is larger than the distance for forming a disulfide bond. Therefore, the present invention attempts to add a cysteine in both the N terminal and the C terminal, and add a glycine, which is a small molecule, or a proline, which renders angular deflection for long chain structure, in 5' end of the added cysteine in the C terminal, so as to decrease the spatial distance between the N terminal and the C terminal and generate a disulfide bond. Accordingly, the N terminal and the C terminal of the protein could be further stabilized, and thus the thermostability of the protein could be improved. In other word, two modifications are performed in the present invention. One is to add a cysteine in the N terminal and add a glycine and a cysteine in the C terminal, and the other one is to add a cysteine in the N terminal and add a proline and a cysteine in the C terminal. The modified proteins include 330 amino acids. The added cysteine in the N terminal is located at position 1 in the amino acid sequence, the added glycine or proline in the C terminal is located at position 329 in the amino acid sequence, and the added cysteine in the C terminal is located at position 330 in the amino acid sequence. Therefore, the first modification is represented as C1G329C330, and the modified protein is called the CGC cellulase. The second modification is represented as C1P329C330, and the modified protein is called CPC cellulase.

The enzyme modification processes and the resulted cellulase proteins are described in detail as follows.

Figure 5:
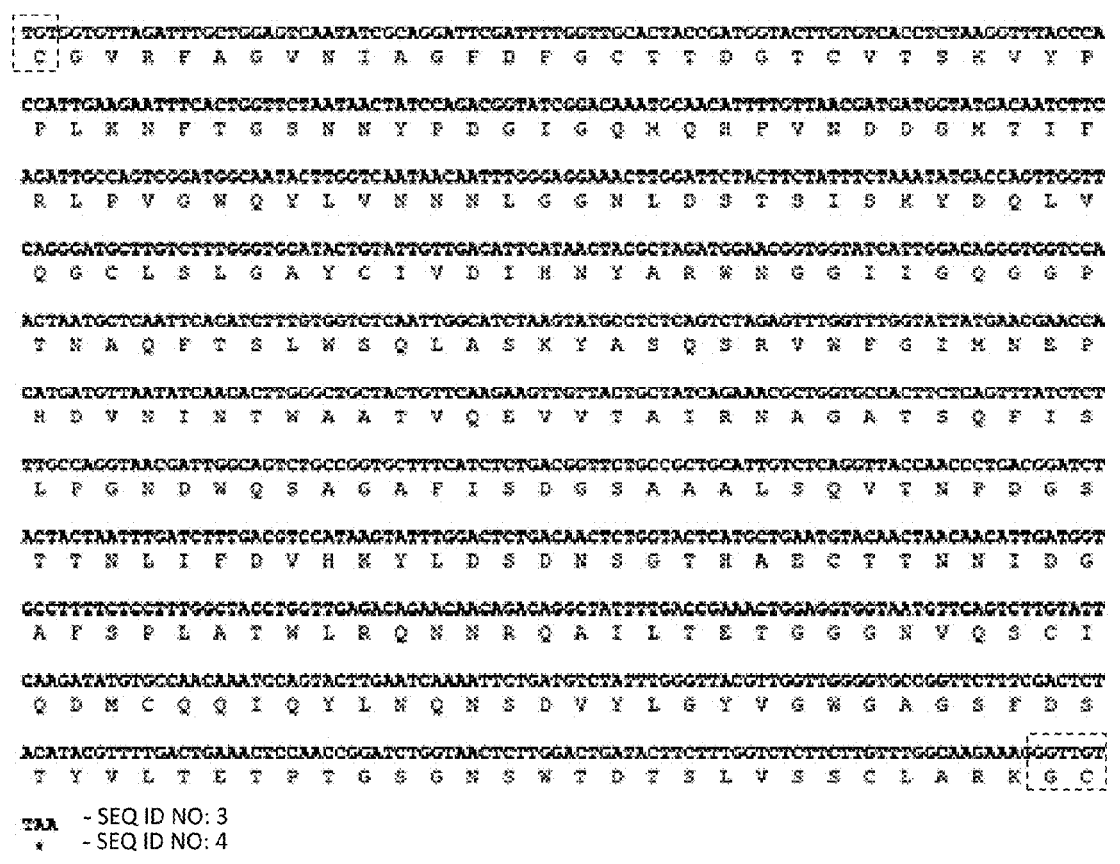
Figure 6:
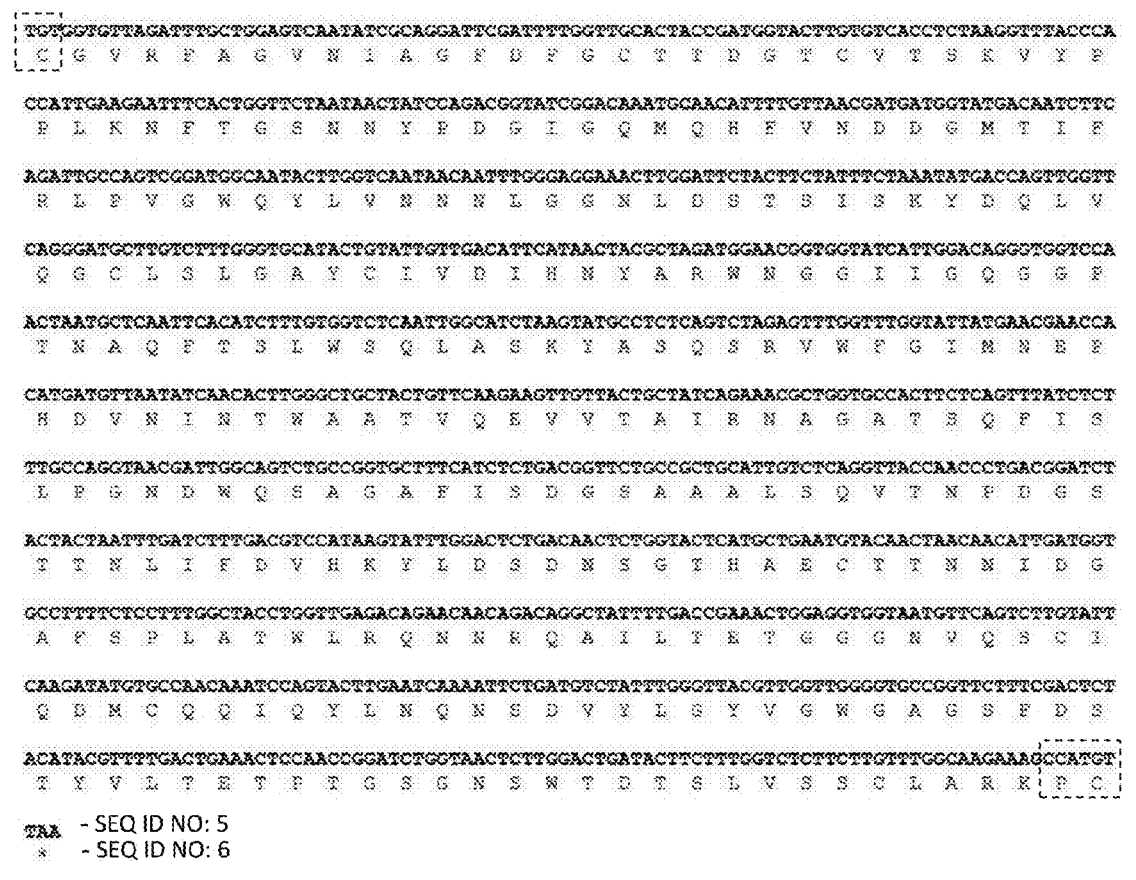

The modifications were performed by site-directed mutagenesis. First, the primer pair I shown in FIG. 2 was used to add a cysteine in the N terminal, in which the forward primer C1 F was numbered as SEQ ID NO: 7 and the reverse primer C1 R was numbered as SEQ ID NO: 8. Subsequently, the primer pair II shown in FIG. 3 was used to add a glycine and a cysteine in the C terminal, in which the forward primer G329C330 F was numbered as SEQ ID NO: 9 and the reverse primer G329C330 R was numbered as SEQ ID NO: 10, so as to obtain the modified C1G329C330 gene of the CGC cellulase. Then, the primer pair III shown in FIG. 4 was used to substitute the glycine at position 329 in the modified C1G329C330 gene with a proline, in which the forward primer P329 F was numbered as SEQ ID NO: 11 and the reverse primer P329 R was numbered as SEQ ID NO: 12, so as to obtain the modified C1P329C330 gene of the CPC cellulase. FIG. 5 shows the nucleotide sequence and the amino acid sequence of the CGC cellulase, wherein the CGC cellulase gene consists of 993 base pairs (SEQ ID NO: 3, including the stop codon) and encodes 330 amino acids (SEQ ID NO: 4). FIG. 6 shows the nucleotide sequence and the amino acid sequence of the CPC cellulase, wherein the CPC cellulase gene consists of 993 base pairs (SEQ ID NO: 5, including the stop codon) and encodes 330 amino acids (SEQ ID NO: 6).

The modified DNA plasmids were linearized by Pme I and then transformed into *Pichia pastoris* X33 by electroporation. The transformants were selected on YPD plates containing 100 μg/ml zeocin and cultured at 30° C. for 2 days. The selected colonies were inoculated in 5 ml of YPD at 30° C. and then amplified in 50 ml of BMGY at 30° C. for 24 hr. The cells were harvested and then resuspended in 20 ml of BMMY to induce protein expression for 4 days. The samples were collected at different time points for every 24 hours, and meanwhile, the methanol was added into the flask to the final concentration of 0.5%. The cells were harvested by centrifugation at 3500 rpm and the supernatant was collected for protein purification and activity determination.

The cellulase activity was determined as follows. The reaction was started by mixing 0.2 ml of 1% carboxymethyl cellulose (CMC, pH 4.8, 0.05 M sodium citrate buffer) and 0.2 ml of the cellulase protein solution at a proper concentration diluted in 0.05 M sodium citrate buffer, pH 4.8. After incubation at 50° C. for 15 min, the reaction was stopped by adding 1.2 ml of 1% DNS reagent and incubation in 100° C. boiled water for 5 min. After cooled down in cold water bath for 10 min, the absorption of OD540 was detected and the enzyme activity was determined. The standard curve of the enzyme activity was determined by 0-0.35 μg/ml glucose standard solution, and one unit was defined as the enzyme level that could release 1 μmole product per minute.

For the thermostability analysis, the cellulase protein solutions at proper concentrations diluted in 0.05 M sodium citrate buffer, pH 4.8 were incubated at different temperatures for 2 min. Subsequently, the protein solutions were cooled down at 4° C. for 10 min and then warmed at room temperature for 10 min. Afterward, the enzyme activities at 50° C. were analyzed as aforesaid procedures. The cellulase activities of the proteins without heat treatment (un-treated) were set to 100% and the relative residual activities of the heat-treated proteins were determined.

FIG. 7 shows the thermostability analysis of the wild type (WT) cellulase, the CGC cellulase and the CPC cellulase, wherein the cellulase activities of the un-treated proteins were set to 100%. It was observed that, after heat-treated with 75° C., 80° C. and 85° C. for 2 min, the relative residual activities of the CPC cellulases were 94%, 70% and 74%, respectively, and the relative residual activities of the CGC cellulases were 93%, 68% and 75%, respectively. Meanwhile, the relative residual activities of the wild type cellulases were 66%, 35% and 43%, respectively, which were much lower than those of the CGC cellulases and the CPC cellulases. In other words, the relative residual activities of the two modified cellulases, i.e. the CGC cellulases and the CPC cellulases, were much higher than the wild type cellulase after heat-treated with different temperatures for 2 min, and thus the two modified cellulases have better thermostability and higher industrial value.

On the other hand, the disulfide bonds of the modified cellulases were also evaluated. The wild type cellulase, the CGC cellulase and the CPC cellulase at proper concentrations were added with 10 mM of dithiothreitol (DTT) and then analyzed by 12.5% sodium dodecyl sulfate polyacrylamide gel electrophoresis (SDS-PAGE) to determine if there were added disulfide bonds existed in the modified cellulases.

Figure 8:
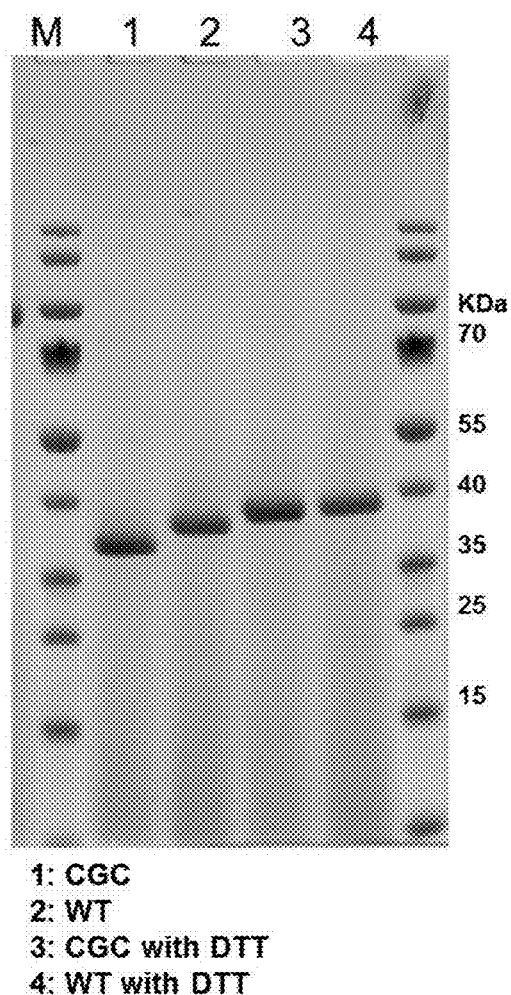
FIG. 8 shows the result of the SDS-PAGE analysis.

FIG. 8 shows the result of the SDS-PAGE analysis, which uses DTT to break the disulfide bonds, and observes the moving speeds of the proteins in the gel. As shown in FIG. 8, the molecular weight of the CGC cellulase with DTT was equivalent to that of the wild type cellulase with DTT, but the position of the CGC cellulase without DTT was significantly lower than that of the wild type cellulase without DTT. That was to say, the modified CGC cellulase included more disulfide bonds, which resulted in a smaller molecular structure, and thus moved faster than the wild type cellulase without increased disulfide bond.

In conclusion, to further increase the industrial value of the cellulase, the present invention modifies the cellulase by rationale engineering to increase the disulfide bond between the N terminal and the C terminal of the protein, so as to stabilize the protein structure and thus improve the thermostability of the cellulase. In the two modification designs, one is to add a cysteine in the N terminal and add a glycine and a cysteine in the C terminal to obtain the CGC cellulase, and the other one is to add a cysteine in the N terminal and add a proline and a cysteine in the C terminal to obtain the CPC cellulase. According to the thermostability analysis, the CGC cellulase and the CPC cellulase have better thermostability than the wild type cellulase, so the CGC cellulase and the CPC cellulase can be more stable when encounter thermal shock, and the production costs thereof can be further reduced. Therefore, the modified cellulases provided in the present invention have increased industrial values.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cellulase comprising a modified amino acid sequence of SEQ ID NO: 2, wherein the modification is adding a cysteine in N terminal and adding a glycine and a cysteine or adding a proline and a cysteine in C terminal.

2. The cellulase according to claim 1 having the full length amino acid sequence of SEQ ID NO: 4.

3. The cellulase according to claim 1 having the full length amino acid sequence of SEQ ID NO: 6.

4. A nucleic acid encoding the cellulase of claim 1.

5. The nucleic acid according to claim 4 wherein a gene encoding the amino acid sequence of SEQ ID NO: 2 is SEQ ID NO: 1.

6. A recombinant plasmid comprising the nucleic acid of claim 4.

* * * * *

SEQUENCE LISTING

```
<160> NUMBER OF SEQ ID NOS: 12

<210> SEQ ID NO 1
<211> LENGTH: 984
<212> TYPE: DNA
<213> ORGANISM: Trichoderma reesei

<400> SEQUENCE: 1
ggtgttagat ttgctggagt caatatcgca ggattcgatt ttggttgcac taccgatggt      60
acttgtgtca cctctaaggt ttacccacca ttgaagaatt tcactggttc taataactat     120
ccagacggta tcggacaaat gcaacatttt gttaacgatg atggtatgac aatcttcaga     180
ttgccagtcg gatggcaata cttggtcaat aacaatttgg gaggaaactt ggattctact     240
tctatttcta aatatgacca gttggttcag ggatgcttgt ctttgggtgc atactgtatt     300
gttgacattc ataactacgc tagatggaac ggtggtatca ttggacaggg tggtccaact     360
aatgctcaat tcacatcttt gtggtctcaa ttggcatcta agtatgcctc tcagtctaga     420
gtttggtttg gtattatgaa cgaaccacat gatgttaata tcaacacttg ggctgctact     480
gttcaagaag ttgttactgc tatcagaaac gctggtgcca cttctcagtt tatctctttg     540
ccaggtaacg attggcagtc tgccggtgct ttcatctctg acggttctgc cgctgcattg     600
tctcaggtta ccaaccctga cggatctact actaatttga tctttgacgt ccataagtat     660
ttggactctg acaactctgg tactcatgct gaatgtacaa ctaacaacat tgatggtgcc     720 tttttctcctt tggctacctg gttgagacag aacaacagac aggctatttt gaccgaaact     780
ggaggtggta atgttcagtc ttgtattcaa gatatgtgcc aacaaatcca gtacttgaat     840
caaaattctg atgtctattt gggttacgtt ggttggggtg ccggttcttt cgactctaca     900
tacgttttga ctgaaactcc aaccggatct ggtaactctt ggactgatac ttctttggtc     960
tcttcttgtt tggcaagaaa gtaa                                            984

<210> SEQ ID NO 2
<211> LENGTH: 327
<212> TYPE: PRT
<213> ORGANISM: Trichoderma reesei

<400> SEQUENCE: 2

Gly Val Arg Phe Ala Gly Val Asn Ile Ala Gly Phe Asp Phe Gly
```

```
              1               5              10              15
            Cys Thr Thr Asp Gly Thr Cys Val Thr Ser Lys Val Tyr Pro Pro
                             20                  25                  30

Leu Lys Asn Phe Thr Gly Ser Asn Asn Tyr Pro Asp Gly Ile Gly
                             35                  40                  45

Gln Met Gln His Phe Val Asn Asp Asp Gly Met Thr Ile Phe Arg
                             50                  55                  60

Leu Pro Val Gly Trp Gln Tyr Leu Val Asn Asn Asn Leu Gly Gly
                             65                  70                  75

Asn Leu Asp Ser Thr Ser Ile Ser Lys Tyr Asp Gln Leu Val Gln
                             80                  85                  90

Gly Cys Leu Ser Leu Gly Ala Tyr Cys Ile Val Asp Ile His Asn
                             95                 100                 105

Tyr Ala Arg Trp Asn Gly Gly Ile Ile Gly Gln Gly Gly Pro Thr
                            110                 115                 120

Asn Ala Gln Phe Thr Ser Leu Trp Ser Gln Leu Ala Ser Lys Tyr
                            125                 130                 135

Ala Ser Gln Ser Arg Val Trp Phe Gly Ile Met Asn Glu Pro His
                            140                 145                 150

Asp Val Asn Ile Asn Thr Trp Ala Ala Thr Val Gln Glu Val Val
                            155                 160                 165

Thr Ala Ile Arg Asn Ala Gly Ala Thr Ser Gln Phe Ile Ser Leu
                            170                 175                 180

Pro Gly Asn Asp Trp Gln Ser Ala Gly Ala Phe Ile Ser Asp Gly
                            185                 190                 195

Ser Ala Ala Ala Leu Ser Gln Val Thr Asn Pro Asp Gly Ser Thr
                            200                 205                 210

Thr Asn Leu Ile Phe Asp Val His Lys Tyr Leu Asp Ser Asp Asn
                            215                 220                 225

Ser Gly Thr His Ala Glu Cys Thr Thr Asn Asn Ile Asp Gly Ala
                            230                 235                 240

Phe Ser Pro Leu Ala Thr Trp Leu Arg Gln Asn Asn Arg Gln Ala
                            245                 250                 255

Ile Leu Thr Glu Thr Gly Gly Gly Asn Val Gln Ser Cys Ile Gln
                            260                 265                 270

Asp Met Cys Gln Gln Ile Gln Tyr Leu Asn Gln Asn Ser Asp Val
                            275                 280                 285

Tyr Leu Gly Tyr Val Gly Trp Gly Ala Gly Ser Phe Asp Ser Thr
                            290                 295                 300

Tyr Val Leu Thr Glu Thr Pro Thr Gly Ser Gly Asn Ser Trp Thr
                            305                 310                 315

Asp Thr Ser Leu Val Ser Ser Cys Leu Ala Arg Lys
                            320                 325

<210> SEQ ID NO 3
<211> LENGTH: 993
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 3
tgtggtgtta gatttgctgg agtcaatatc gcaggattcg attttggttg cactaccgat     60
ggtacttgtg tcacctctaa ggtttaccca ccattgaaga atttcactgg ttctaataac    120
```

```
tatccagacg gtatcggaca aatgcaacat tttgttaacg atgatggtat gacaatcttc     180
agattgccag tcggatggca atacttggtc aataacaatt tgggaggaaa cttggattct     240
acttctattt ctaaatatga ccagttggtt cagggatgct tgtctttggg tgcatactgt     300
attgttgaca ttcataacta cgctagatgg aacggtggta tcattggaca gggtggtcca     360
actaatgctc aattcacatc tttgtggtct caattggcat ctaagtatgc ctctcagtct     420
agagtttggt ttggtattat gaacgaacca catgatgtta atatcaacac ttgggctgct     480
actgttcaag aagttgttac tgctatcaga aacgctggtg ccacttctca gtttatctct     540
ttgccaggta acgattggca gtctgccggt gctttcatct ctgacggttc tgccgctgca     600
ttgtctcagg ttaccaaccc tgacggatct actactaatt tgatctttga cgtccataag     660
tatttggact ctgacaactc tggtactcat gctgaatgta caactaacaa cattgatggt     720
gccttttctc ctttggctac ctggttgaga cagaacaaca gacaggctat tttgaccgaa     780
actggaggtg gtaatgttca gtcttgtatt caagatatgt gccaacaaat ccagtacttg     840
aatcaaaatt ctgatgtcta tttgggttac gttggttggg gtgccggttc tttcgactct     900
acatacgttt tgactgaaac tccaaccgga tctggtaact cttggactga tacttctttg     960
gtctcttctt gtttggcaag aaagggttgt taa                                 993
```

<210> SEQ ID NO 4
<211> LENGTH: 330
<212> TYPE: PRT
<213> ORGANISM: Artificial Sequence
<220> FEATURE:
<223> OTHER INFORMATION: Sequence synthetically translated from SEQ ID
      NO: 3

<400> SEQUENCE: 4

```
Cys Gly Val Arg Phe Ala Gly Val Asn Ile Ala Gly Phe Asp Phe
 1               5                  10                  15

Gly Cys Thr Thr Asp Gly Thr Cys Val Thr Ser Lys Val Tyr Pro
                20                  25                  30

Pro Leu Lys Asn Phe Thr Gly Ser Asn Asn Tyr Pro Asp Gly Ile
                35                  40                  45

Gly Gln Met Gln His Phe Val Asn Asp Gly Met Thr Ile Phe
                50                  55                  60

Arg Leu Pro Val Gly Trp Gln Tyr Leu Val Asn Asn Asn Leu Gly
                65                  70                  75

Gly Asn Leu Asp Ser Thr Ser Ile Ser Lys Tyr Asp Gln Leu Val
                80                  85                  90

Gln Gly Cys Leu Ser Leu Gly Ala Tyr Cys Ile Val Asp Ile His
                95                  100                 105

Asn Tyr Ala Arg Trp Asn Gly Gly Ile Ile Gly Gln Gly Gly Pro
                110                 115                 120

Thr Asn Ala Gln Phe Thr Ser Leu Trp Ser Gln Leu Ala Ser Lys
                125                 130                 135

Tyr Ala Ser Gln Ser Arg Val Trp Phe Gly Ile Met Asn Glu Pro
                140                 145                 150

His Asp Val Asn Ile Asn Thr Trp Ala Ala Thr Val Gln Glu Val
                155                 160                 165

Val Thr Ala Ile Arg Asn Ala Gly Ala Thr Ser Gln Phe Ile Ser
                170                 175                 180

Leu Pro Gly Asn Asp Trp Gln Ser Ala Gly Ala Phe Ile Ser Asp
```

```
                  185                 190                 195
Gly Ser Ala Ala Ala Leu Ser Gln Val Thr Asn Pro Asp Gly Ser
            200                 205                 210
Thr Thr Asn Leu Ile Phe Asp Val His Lys Tyr Leu Asp Ser Asp
            215                 220                 225
Asn Ser Gly Thr His Ala Glu Cys Thr Thr Asn Ile Asp Gly
            230                 235                 240
Ala Phe Ser Pro Leu Ala Thr Trp Leu Arg Gln Asn Asn Arg Gln
            245                 250                 255
Ala Ile Leu Thr Glu Thr Gly Gly Gly Asn Val Gln Ser Cys Ile
            260                 265                 270
Gln Asp Met Cys Gln Gln Ile Gln Tyr Leu Asn Gln Asn Ser Asp
            275                 280                 285
Val Tyr Leu Gly Tyr Val Gly Trp Gly Ala Gly Ser Phe Asp Ser
            290                 295                 300
Thr Tyr Val Leu Thr Glu Thr Pro Thr Gly Ser Gly Asn Ser Trp
            305                 310                 315
Thr Asp Thr Ser Leu Val Ser Ser Cys Leu Ala Arg Lys Gly Cys
            320                 325                 330
```

<210> SEQ ID NO 5
<211> LENGTH: 993
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5

```
tgtggtgtta gatttgctgg agtcaatatc gcaggattcg attttggttg cactaccgat      60
ggtacttgtg tcacctctaa ggtttaccca ccattgaaga atttcactgg ttctaataac     120
tatccagacg gtatcggaca aatgcaacat tttgttaacg atgatggtat gacaatcttc     180
agattgccag tcggatggca atacttggtc aataacaatt gggaggaaa cttggattct     240
acttctattt ctaaatatga ccagttggtt cagggatgct gtctctttgg tgcatactgt     300
attgttgaca ttcataacta cgctagatgg aacggtggta tcattggaca gggtggtcca     360
actaatgctc aattcacatc tttgtggtct caattggcat ctaagtatgc ctctcagtct     420
agagtttggt ttggtattat gaacgaacca catgatgtta atatcaacac ttgggctgct     480
actgttcaag aagttgttac tgctatcaga aacgctggtg ccacttctca gtttatctct     540
ttgccaggta acgattggca gtctgccggt gctttcatct ctgacggttc tgccgctgca     600
ttgtctcagg ttaccaaccc tgacggatct actactaatt tgatctttga cgtccataag     660
tatttggact ctgacaactc tggtactcat gctgaatgta caactaacaa cattgatggt     720
gccttttctc ctttggctac ctggttgaga cagaacaaca gacaggctat tttgaccgaa     780
actggaggtg gtaatgttca gtcttgtatt caagatatgt gccaacaaat ccagtacttg     840
aatcaaaatt ctgatgtcta tttgggttac gttggttggg gtgccggttc tttcgactct     900
acatacgttt tgactgaaac tccaaccgga tctggtaact cttggactga tacttctttg     960
gtctcttctt gtttggcaag aaagccatgt taa                                   993
```

<210> SEQ ID NO 6
<211> LENGTH: 330
<212> TYPE: PRT
<213> ORGANISM: Artificial Sequence
<220> FEATURE:
<223> OTHER INFORMATION: Sequence synthetically translated from SEQ ID
      NO: 5

<400> SEQUENCE: 6

```
Cys Gly Val Arg Phe Ala Gly Val Asn Ile Ala Gly Phe Asp Phe
1               5                   10                  15

Gly Cys Thr Thr Asp Gly Thr Cys Val Thr Ser Lys Val Tyr Pro
                20                  25                  30

Pro Leu Lys Asn Phe Thr Gly Ser Asn Asn Tyr Pro Asp Gly Ile
                35                  40                  45

Gly Gln Met Gln His Phe Val Asn Asp Asp Gly Met Thr Ile Phe
                50                  55                  60

Arg Leu Pro Val Gly Trp Gln Tyr Leu Val Asn Asn Asn Leu Gly
                65                  70                  75

Gly Asn Leu Asp Ser Thr Ser Ile Ser Lys Tyr Asp Gln Leu Val
                80                  85                  90

Gln Gly Cys Leu Ser Leu Gly Ala Tyr Cys Ile Val Asp Ile His
                95                  100                 105

Asn Tyr Ala Arg Trp Asn Gly Gly Ile Ile Gly Gln Gly Gly Pro
                110                 115                 120

Thr Asn Ala Gln Phe Thr Ser Leu Trp Ser Gln Leu Ala Ser Lys
                125                 130                 135

Tyr Ala Ser Gln Ser Arg Val Trp Phe Gly Ile Met Asn Glu Pro
                140                 145                 150

His Asp Val Asn Ile Asn Thr Trp Ala Ala Thr Val Gln Glu Val
                155                 160                 165

Val Thr Ala Ile Arg Asn Ala Gly Ala Thr Ser Gln Phe Ile Ser
                170                 175                 180

Leu Pro Gly Asn Asp Trp Gln Ser Ala Gly Ala Phe Ile Ser Asp
                185                 190                 195

Gly Ser Ala Ala Ala Leu Ser Gln Val Thr Asn Pro Asp Gly Ser
                200                 205                 210

Thr Thr Asn Leu Ile Phe Asp Val His Lys Tyr Leu Asp Ser Asp
                215                 220                 225

Asn Ser Gly Thr His Ala Glu Cys Thr Thr Asn Asn Ile Asp Gly
                230                 235                 240

Ala Phe Ser Pro Leu Ala Thr Trp Leu Arg Gln Asn Asn Arg Gln
                245                 250                 255

Ala Ile Leu Thr Glu Thr Gly Gly Gly Asn Val Gln Ser Cys Ile
                260                 265                 270

Gln Asp Met Cys Gln Gln Ile Gln Tyr Leu Asn Gln Asn Ser Asp
                275                 280                 285

Val Tyr Leu Gly Tyr Val Gly Trp Gly Ala Gly Ser Phe Asp Ser
                290                 295                 300

Thr Tyr Val Leu Thr Glu Thr Pro Thr Gly Ser Gly Asn Ser Trp
                305                 310                 315

Thr Asp Thr Ser Leu Val Ser Ser Cys Leu Ala Arg Lys Pro Cys
                320                 325                 330
```

<210> SEQ ID NO 7
<211> LENGTH: 34
<212> TYPE: DNA
<213> ORGANISM: Artificial Sequence
<220> FEATURE:
<223> OTHER INFORMATION: Synthetically generated primer

```
<400> SEQUENCE: 7
gctgaagctg aattctgtgg tgttagattt gctg                              34

<210> SEQ ID NO 8
<211> LENGTH: 34
<212> TYPE: DNA
<213> ORGANISM: Artificial Sequence
<220> FEATURE:
<223> OTHER INFORMATION: Synthetically generated primer

<400> SEQUENCE: 8
cagcaaatct aacaccacag aattcagctt cagc                              34

<210> SEQ ID NO 9
<211> LENGTH: 41
<212> TYPE: DNA
<213> ORGANISM: Artificial Sequence
<220> FEATURE:
<223> OTHER INFORMATION: Synthetically generated primer

<400> SEQUENCE: 9
ttgtttggca agaaagggtt gttaagcggc cgccagcttt c                      41

<210> SEQ ID NO 10
<211> LENGTH: 41
<212> TYPE: DNA
<213> ORGANISM: Artificial Sequence
<220> FEATURE:
<223> OTHER INFORMATION: Synthetically generated primer

<400> SEQUENCE: 10
gaaagctggc ggccgcttaa caacccttc ttgccaaaca a                       41

<210> SEQ ID NO 11
<211> LENGTH: 35
<212> TYPE: DNA
<213> ORGANISM: Artificial Sequence
<220> FEATURE:
<223> OTHER INFORMATION: Synthetically generated primer

<400> SEQUENCE: 11
ttgtttggca agaaagccat gttaagcggc cgcca                             35

<210> SEQ ID NO 12
<211> LENGTH: 35
<212> TYPE: DNA
<213> ORGANISM: Artificial Sequence
<220> FEATURE:
<223> OTHER INFORMATION: Synthetically generated primer

<400> SEQUENCE: 12
aaagctggcg gccgcttaac atggctttct tgcca                             35
```